(12) United States Patent
Huddar et al.

(10) Patent No.: US 11,011,274 B2
(45) Date of Patent: May 18, 2021

(54) METHOD AND APPARATUS FOR PREDICTING MORTALITY OF A PATIENT USING TRAINED CLASSIFIERS

(71) Applicant: Conduent Business Services, LLC, Dallas, TX (US)

(72) Inventors: Vijay Huddar, Bijapur (IN); Bhupendra Solanki, Indore (IN); Vaibhav Rajan, Kammanahalli (IN); Sakyajit Bhattacharya, Koramangala (IN)

(73) Assignee: CONDUENT BUSINESS SERVICES, LLC, Dallas, TX (US)

( * ) Notice: Subject to any disclaimer, the term of this patent is extended or adjusted under 35 U.S.C. 154(b) by 818 days.

(21) Appl. No.: 15/065,432

(22) Filed: Mar. 9, 2016

(65) Prior Publication Data

US 2017/0262597 A1 Sep. 14, 2017

(51) Int. Cl.
| | |
|---|---|
| *G06N 20/00* | (2019.01) |
| *G06N 20/20* | (2019.01) |
| *G16H 50/20* | (2018.01) |
| *G06F 19/00* | (2018.01) |

(52) U.S. Cl.
CPC ............. *G16H 50/20* (2018.01); *G06F 19/00* (2013.01); *G06N 20/00* (2019.01); *G06N 20/20* (2019.01)

(58) Field of Classification Search
CPC ...... G06N 99/005; G06N 5/025; G06N 7/005; G06N 20/00; G06K 9/6256; G06K 9/6269
USPC .......................................................... 706/12
See application file for complete search history.

(56) References Cited

U.S. PATENT DOCUMENTS

| | | | |
|---|---|---|---|
| 9,267,954 B2* | 2/2016 | Wienhues-Thelen | ...................... G01N 33/6887 |
| 9,764,162 B1* | 9/2017 | Willcut | ................. A61B 6/032 |
| 10,234,462 B2* | 3/2019 | Block | ................. G01N 33/6893 |
| 10,390,765 B1* | 8/2019 | McNair | ................ A61B 5/0015 |
| 2007/0129983 A1* | 6/2007 | Scherpbier | ............. G06Q 50/22 705/2 |
| 2009/0018864 A1* | 1/2009 | Gecelter | ................ G16H 40/20 705/2 |

(Continued)

OTHER PUBLICATIONS

Singh et al., Incorporating Temporal EHR Data in Predictive Models for Risk Stratification of Renal Function Deterioration, J. of Biomedical Informatics vol. 53 (Feb. 2015) at p. 220-228 (Year: 2015).*

(Continued)

*Primary Examiner* — Viker A Lamardo

(57) ABSTRACT

A method, non-transitory computer readable medium and apparatus for predicting mortality of a current patient are disclosed. For example, the method includes receiving data associated with a plurality of different patients with known mortality outcomes, wherein the data includes a subset of data for each one of a plurality of different measurement timepoints for each one of the plurality of different patients, calculating n number of classifiers, wherein n is equal to a number of the plurality of different measurement timepoints, receiving data associated with the current patient at an i-th measurement timepoint, predicting the current patient has a high mortality risk based on an output of the i-th classifier of the n number of classifiers and transmitting a signal to a health administration server to cause an alarm to be generated in response to the high mortality risk that is predicted.

15 Claims, 3 Drawing Sheets

(56) References Cited

U.S. PATENT DOCUMENTS

| | | | | |
|---|---|---|---|---|
| 2009/0125337 A1* | 5/2009 | Abri | ............... | G16H 40/20 |
| | | | | 705/3 |
| 2009/0234672 A1* | 9/2009 | Dicks | ............... | G16H 15/00 |
| | | | | 705/3 |
| 2013/0066647 A1* | 3/2013 | Andrie | ............... | G06Q 10/10 |
| | | | | 705/2 |
| 2015/0213227 A1* | 7/2015 | Vairavan | ............... | G16H 50/20 |
| | | | | 706/12 |
| 2016/0135706 A1* | 5/2016 | Sullivan | ............... | A61B 5/1118 |
| | | | | 600/301 |
| 2016/0350499 A1* | 12/2016 | Anjomshoa | ............ | G16H 40/20 |
| 2016/0364862 A1* | 12/2016 | Reicher | ............... | A61B 5/7267 |

OTHER PUBLICATIONS

Ghose et al., An Improved Patient-Specific Mortality Risk Prediction in ICU in a Random Forest Classification Framework, IOS Press (Jul. 2015) at pp. 56-61. (Year: 2015).*

Wagner & Draper, Acute Physiology and Chronic Health Evaluation (APACHE II) and Medicare Reimbursement, Health Care Finance Rev, Suppl. (1984) at p. 91-105. (Year: 1984).*

Tang et al., A Comparison of Imputation Methods in a Longitudinal Randomized Clinical Trial, Statistics in Medicine vol. 24 at p. 2111-2128 (2005) (Year: 2005).*

Azur et al., Multiple Imputation by Chained Equations: What is it and how does it work?, Int J Methods Psychiatr Res. vol. 20 (2011) at p. 40-49 (Year: 2011).*

Burch et al.—"Modified early warning score predicts the need for hospital admission and inhospital mortality"—2008—https://search.proquest.com/docview/1780012318?accountid=14753&pq-origsite=360link (Year: 2008).*

Hammond et al.—"The effect of implementing a modified early warning scoring (MEWS) system onthe adequacy of vital sign documentation"—2013—https://www.sciencedirect.com/science/article/pii/S103673141200077X (Year: 2013).*

* cited by examiner

METHOD AND APPARATUS FOR PREDICTING MORTALITY OF A PATIENT USING TRAINED CLASSIFIERS

The present disclosure relates generally to patient monitoring and care and, more particularly, to a method and apparatus for predicting mortality of a patient.

BACKGROUND

An intensive care unit (ICU) has the most critically ill patients who are continuously monitored to check for disease progression and potential complications. As the need for ICUs have grown worldwide, more ICUs have been created but the availability of resources in ICUs are becoming increasingly scarce.

Whether or not a patient will survive in the ICU is an important determination to assist clinical staff in possible course of action for the patient. Critical decisions during ICU stay such as interrupting treatments or providing Do-Not-Resuscitate orders affect not only the care given to ICU patients but also the availability of ICU resources to other patients in need by enabling patient triage through prioritized care to high mortality risk patients.

Some scoring systems such as the acute physiology and chronic health evaluation system (APACHE II), the simplified acute physiology score (SAPS II), mortality probability model (MPM), and sequential organ failure assessment score (SOFA) exist. However, these scoring systems can sometimes be inaccurate due to the need for values of specific investigations or conditions (e.g., presence of a ventilator) of the patient. These investigations may not always be performed and the conditions may not always be recorded in the Electronic Medical Records (EMRs) making the scoring systems unreliable and difficult to automate in Clinical Decision Support Systems.

SUMMARY

According to aspects illustrated herein, there are provided a method, non-transitory computer readable medium and apparatus for predicting mortality of a current patient. One disclosed feature of the embodiments is a method that receives data associated with a plurality of different patients with known mortality outcomes, wherein the data includes a subset of data for each one of a plurality of different measurement timepoints for each one of the plurality of different patients, wherein the data is received via a communication session to a plurality of vital measurement devices and a server storing lab measurements, calculates n number of classifiers, wherein n is equal to a number of the plurality of different measurement timepoints, receives data associated with the current patient at an i-th measurement timepoint, predicts the current patient has a high mortality risk based on an output of the i-th classifier of the n number of classifiers, wherein the output is based on the i-th classifier processing the data associated with the current patient and transmits a signal to a health administration server to cause an alarm to be generated in response to the high mortality risk that is predicted.

Another disclosed feature of the embodiments is a non-transitory computer-readable medium having stored thereon a plurality of instructions, the plurality of instructions including instructions which, when executed by a processor, cause the processor to perform operations that receive data associated with a plurality of different patients with known mortality outcomes, wherein the data includes a subset of data for each one of a plurality of different measurement timepoints for each one of the plurality of different patients, wherein the data is received via a communication session to a plurality of vital measurement devices and a server storing lab measurements, calculate n number of classifiers, wherein n is equal to a number of the plurality of different measurement timepoints, receive data associated with the current patient at an i-th measurement timepoint, predict the current patient has a high mortality risk based on an output of the i-th classifier of the n number of classifiers, wherein the output is based on the i-th classifier processing the data associated with the current patient and transmit a signal to a health administration server to cause an alarm to be generated in response to the high mortality risk that is predicted.

Another disclosed feature of the embodiments is an apparatus comprising a processor and a computer-readable medium storing a plurality of instructions which, when executed by the processor, cause the processor to perform operations that receive data associated with a plurality of different patients with known mortality outcomes, wherein the data includes a subset of data for each one of a plurality of different measurement timepoints for each one of the plurality of different patients, wherein the data is received via a communication session to a plurality of vital measurement devices and a server storing lab measurements, calculate n number of classifiers, wherein n is equal to a number of the plurality of different measurement timepoints, receive data associated with the current patient at an i-th measurement timepoint, predict the current patient has a high mortality risk based on an output of the i-th classifier of the n number of classifiers, wherein the output is based on the i-th classifier processing the data associated with the current patient and transmit a signal to a health administration server to cause an alarm to be generated in response to the high mortality risk that is predicted.

BRIEF DESCRIPTION OF THE DRAWINGS

The teaching of the present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

The present disclosure broadly discloses a method and apparatus for predicting mortality of a current patient. As discussed above, some scoring systems exist for determining whether a patient will survive. However, these scoring systems can sometimes be inaccurate due to the need for values of specific investigations or conditions of the patient. These investigations may not always be performed and the conditions may not always be recorded in the Electronic Medical Records (EMRs) making the scoring systems unreliable and difficult to automate in Clinical Decision Support Systems.

Embodiments of the present disclosure provide a novel method and apparatus to accurately predict mortality of a patient in an intensive care unit (ICU). The present disclosure identifies a specific set of features that can be used to train a classifier. In addition, a classifier may be trained for each measurement timepoint. Notably, at different points, different measurements of various vitals or labs may be measured for a patient in the ICU. In addition, the probability of predicting mortality or survival may be different at each different measurement timepoint for the patient in the ICU.

The embodiments of the present disclosure deploy a fully automated system for collecting the data used to train the classifier. The identified features use data that can be automatically obtained from a vital measurement device connected to the patient and a communication network or a server that stores lab measurements of the patient, such as an Electronic Medical Records database. In other words, the embodiments of the present disclosure do not rely on specific investigations or conditions of the patient that require a manual observation.

Figure 1:
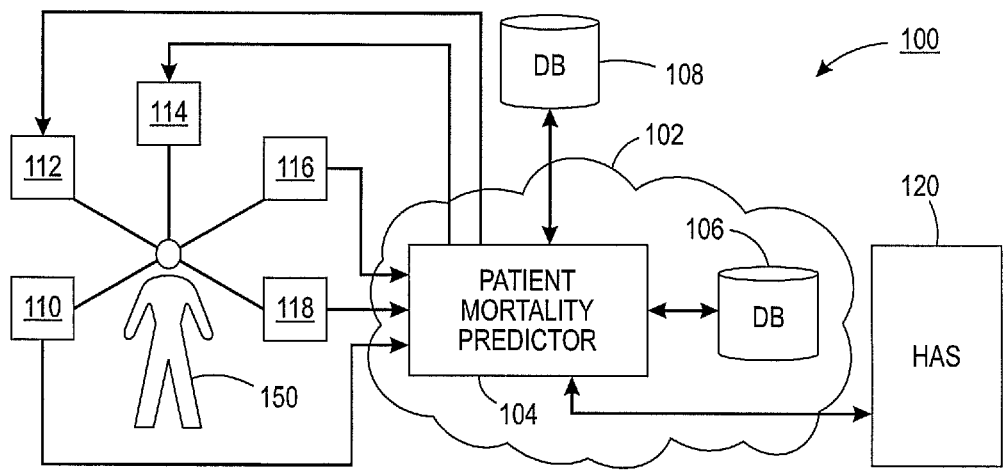
FIG. 1 illustrates an example block diagram of a communication network of the present disclosure.

FIG. 1 illustrates an example system 100 of the present disclosure. In one embodiment, the system 100 may include a communication network 102. The communication network 102 may be any type of wired or wireless communication network. In one embodiment, the communication network 100 may be an Internet Protocol (IP) network.

It should be noted that the communication network 102 has been simplified for ease of explanation. For example, the communication network 102 may include one or more additional network elements (e.g., a router, a gateway, a border element, switches, and the like) or access networks (e.g., a cellular access network, a broadband access network, and the like) that are not shown.

In one embodiment, the communication network 102 may include a patient mortality predictor 104 and a database (DB) 106. In one example, the patient mortality predictor 104 may collect patient data, process the data, train one or more classifiers and apply the classifiers to data associated with one or more current patients to predict whether the current patients are a high risk for mortality. The functions and operations of the patient mortality predictor 104 are described in further detail below in FIGS. 2-4. In one embodiment, the DB 106 may store the data that is collected and the classifiers that are generated.

In one embodiment, the classifiers may be trained using data associated with previous patients that have known mortality outcomes. In other words, data collected from previous patients that were in the ICU that have either survived and have been discharged, or did not survive, can be used to train the classifiers. The classifiers can then be used to predict whether a current patient will survive. The data may be received from one or more DBs 108. The DB 108 may be a third party database (e.g., from hospitals around the country) or a database of a hospital that has deployed the patient mortality predictor 104.

In one embodiment, the data may include subsets of data for each one of a plurality of different measurement timepoints for each one of the previous patients. The different subsets of data can be used to train a classifier for each one of the plurality of different measurement timepoints. In other words, a plurality of classifiers may be trained, wherein each one of the plurality of classifiers is associated with one of the plurality of different measurement timepoints.

In one embodiment, the different measurement timepoints may refer to an instance when a particular set of measurements of a patient are taken. The timepoints may have an associated time stamp, but are not necessarily correlated to an exact time period. For example, a first measurement timepoint may be when a patient first arrives at the ICU. A second measurement timepoint may be after a particular lab measurement is conducted. A third measurement timepoint may be after 24 hours in the ICU, and so forth. A unique classifier may be trained for each different measurement timepoint based on the subset of data associated with a particular measurement timepoint.

In one embodiment, a current patient 150 may be admitted to the ICU. The current patient 150 may be connected to a plurality of vital measurement devices 110, 112, 114, 116 and 118. Although five vital measurement devices are illustrated in FIG. 1, it should be noted that any number of vital measurement devices may be deployed. In one embodiment, the vital measurement devices 110, 112, 114, 116 and 118 may automatically collect vital measurements of the current patient 150 that are used by the patient mortality predictor 104.

For example, the vital measurement device 110 may measure blood pressure (e.g., systolic blood pressure and diastolic blood pressure), the vital measurement device 112 may measure a respiration rate, the vital measurement device 114 may measure a heart rate, the vital measurement device 116 may measure an oxygen saturation and the vital measurement device 118 may measure a temperature. In one embodiment, a plurality of lab measurements may also be taken and stored in a database that is automatically accessible by the patient mortality predictor 104 (e.g., the DB 106). The plurality of lab measurements may include arterial blood pH, partial pressure of carbon dioxide, partial pressure of oxygen, sodium, potassium, bicarbonate, blood urea nitrogen, serum creatinine, white blood cell count, hematocrit, platelet count, bilirubin, urine output, low density lipoprotein cholesterol, lactic acid, troponin I, troponin T, random blood glucose, fasting blood glucose, fraction of inspired oxygen, albumin, alkaline, phosphatase, alanine, high density lipoprotein cholesterol and magnesium.

Based on the data collected from the current patient, the patient mortality predictor 104 may predict whether the current patient 150 will survive based on an i-th classifier of n classifiers for an i-th measurement timepoint. If the current patient 150 is predicted to have a high mortality risk, the patient mortality predictor 104 may transmit a signal to a health administration server (HAS) 120 to cause an alarm to be generated. In one embodiment, the patient mortality predictor 104 may continue to predict whether the current patient 150 will survive by applying the i-th classifier for an i-th measurement timepoint for all n measurement timepoints.

In one embodiment, the HAS 120 may be a nurse monitoring station that displays a current status of the current patients in the ICU. If the current patient 150 is determined to be a high mortality risk, an alarm may trigger for the current patient 150 at the HAS 120. In response, one or more communication signals may be sent to endpoint devices of additional doctors or nurses to take immediate medical action.

In one embodiment, the signal from the patient mortality predictor may cause the HAS 120 to automatically schedule appointments for a particular lab, a particular operating room, automatically prescribe a medication, and the like. As a result, precious seconds can be saved from a nurse or doctor recognizing the alarm and manually scheduling the lab, the operating room, prescribing a particular medication, and the like.

In one embodiment, the signal may include a percentage of the high mortality risk as calculated by the i-th classifier. In one embodiment, with each i-th measurement timepoint prediction, the patient mortality predictor 104 may send a percentage that the current patient 150 is likely to be classified as a survivor or a high mortality risk to the HAS 120. In other words, even if the current patient 150 is not identified as a high mortality risk, the patient mortality predictor 104 may still provide the percentages calculated by the i-th classifier for one of binary outcomes of the i-th classifier (e.g., survival or mortality).

Figure 2:
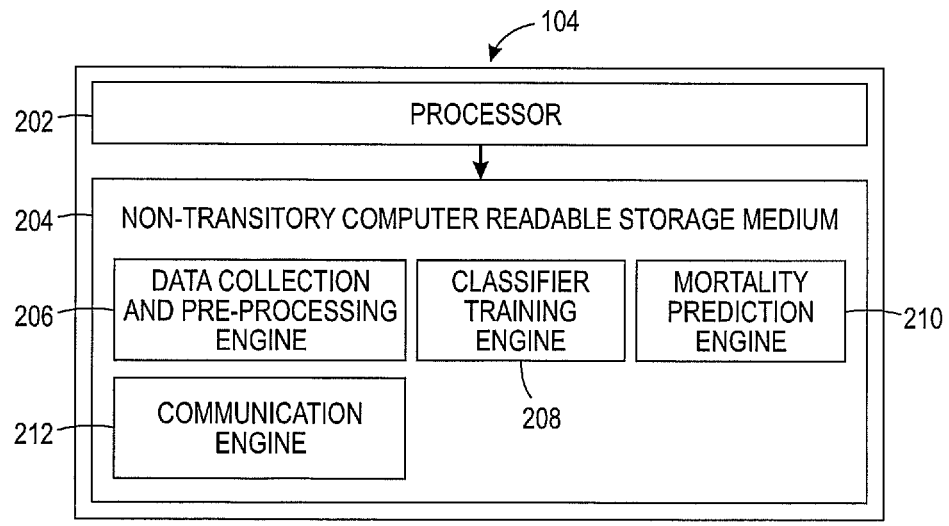
FIG. 2 illustrates an example apparatus of the present disclosure.

FIG. 2 illustrates a high level block diagram of the patient mortality predictor 104. In one embodiment, the patient mortality predictor 104 may include a processor 202 and a non-transitory computer readable storage medium 204. In one embodiment, the non-transitory computer readable storage medium 204 may include instructions that are executed by the processor 202 to perform the functions described herein.

In one embodiment, the non-transitory computer readable storage medium 204 may include a data collection and pre-processing engine 206, a classifier training engine 208, a mortality prediction engine 210 and a communication engine 212. In one embodiment, the data collection and pre-processing engine 206 may perform automatic data collection from the DB 108 that can be used to train the classifiers. In addition, the data collection and pre-processing engine 206 may perform automatic data collection from the DB 106 and the vital measurement devices 110, 112, 114, 116 and 118.

In one embodiment, the data collection and pre-processing engine 206 may also pre-process the data to add missing data for each different measurement timepoint. For example, some vital measurements may be missing from the collected data that is used to train the classifiers, or a lab measurement for the current patient 150 may have been skipped for an i-th measurement timepoint.

In one embodiment, the data collection and pre-processing engine 206 may add the missing data by applying a value for a previous measurement timepoint for the missing data of a current measurement timepoint when the value for the previous measurement timepoint is less than a predefined time period, e.g., four hours old. For example, at the first measurement timepoint a heart rate of 72 beats per minute may have been recorded. At a second measurement timepoint, the heart rate value may be missing (e.g., the heart rate device may have been temporarily disconnected). However, if the heart rate value at the first measurement timepoint is less than four hours old, the heart rate value of the first measurement timepoint may be used as the heart rate value at the second measurement timepoint.

Alternatively, if the value for a previous measurement timepoint for the missing data of a current measurement timepoint is greater than four hours old, the value may be estimated. In one embodiment, the missing data may be estimated using a multivariate imputation by chained equations (MICE) function.

In one embodiment, the classifier training engine 208 may train a plurality of classifiers. The plurality of classifiers may include one classifier for each i-th measurement timepoint. Thus, if there are n measurement timepoints, then the classifier training engine 208 may train n classifiers. The n classifiers may have an i-th classifier for each i-th measurement timepoint.

As discussed above, each classifier for an i-th measurement timepoint may be trained using a subset of data (also referred to $T_i$) of the previous patient that corresponds to the i-th measurement timepoint. In one embodiment, the subset of data may be selected based upon the subsets of data that have the three maximum and three minimum systolic blood pressure (SBP) values and heart rate (HR) values. For example, it has been found that the systolic blood pressure and the heart rate may be the most accurate predictors of patient mortality in the ICU and the classifiers may be trained using features extracted from these selected subsets of data from the overall data set of the previous patients taken at a plurality of different measurement timepoints.

To illustrate, at each different measurement timepoint a patient may have a plurality of vital measurements and a plurality of lab measurements. The patient may have data associated with 20 different measurement timepoints. From the data set a subset of the data may be selected that includes the three highest SBP values and the three lowest SBP values. Similarly, from the data set a subset of the data may be selected that includes the three highest HR values and the three lowest HR values. As a result, 12 different subsets of data may be selected from the overall data set of 20 different measurement timepoints. Each one of the 12 different subsets of data may each include the plurality of vital measurements and the plurality of lab measurements (e.g., 6 vitals and 25 lab measurements for a total of 31 values) that are used to extract the features to train each classifier, as discussed below.

In one embodiment, each one of the classifiers may be trained using a random forest function. For example, a random forest function may include a random forest with 500 trees.

In one embodiment, each one of the n classifiers can be trained based upon features identified or extracted from the subsets of data selected from the data that is collected, as described above. In one embodiment, the features may be based on a plurality of vital measurements, a plurality of lab measurements and demographic information. The plurality of vital measurements may include a systolic blood pressure (SBP), a diastolic blood pressure (DBP), a respiration rate (RR) (e.g., respirations per minute (rpm)), a heart rate (HR) (e.g., beats per minute (bpm)), an oxygen saturation (OSat) and a temperature (temp) (e.g., degrees Celsius (° C.)). The plurality of lab measurements may include arterial blood pH, partial pressure of carbon dioxide, partial pressure of oxygen, sodium, potassium, bicarbonate, blood urea nitrogen, serum creatinine, white blood cell count, hematocrit, platelet count, bilirubin, urine output, low density lipoprotein cholesterol, lactic acid, troponin I, troponin T, random blood glucose, fasting blood glucose, fraction of inspired oxygen, albumin, alkaline, phosphatase, alanine, high density lipoprotein cholesterol and magnesium. The demographic information may include an age and a sex of the patient.

In one embodiment, the features may include 125 features that have been identified that provides a more accurate prediction of mortality. The 125 features may be based off of data that can automatically be collected without any manual observation as required by other mortality prediction methods. For example, the data may include various statistical values of the vital measurements, the lab measurements and the demographic information.

In one embodiment, 25 of the 125 features may be based on a mean, a standard deviation, a maximum value and a minimum value of all six vital measurements and a mean SBP/DBP. In one embodiment, 12 of the 125 features may be based on a difference of a mean of six vitals from a population mean of all patients who survive in $T_i$ and a difference of a mean of six vitals from a population mean of all patients who die in $T_i$. In one embodiment, 24 of the 125 features may be based on the following functions for each of the six vital measurements:

$$\frac{\sum_{p \in P} p}{|P|}, \frac{\sum_{n \in N} n}{|N|}, \frac{|N|}{|P|+|N|} \text{ and } \frac{|P|}{|P|+|N|},$$

where $v_i$ denotes a vital measurement at the i-th measurement timepoint for $t_i$, for a patient, P is the set of consecutive differences $(v_i-v_{i-1})$ where $v_i > v_{i-1}$ and N is the set of consecutive differences $(v_i-v_{i-1})$ where $v_i < v_{i-1}$.

In one embodiment, 5 of the 125 features may be based on a mean modified early warning score (MEWS) of SBP, HR, RR, OSat and temp. MEWS is a score based on the measurement of vitals and the amount by which they deviate from the respective normal ranges as shown in table 1 below. Vital values in the normal range are scored 0 and deviations in either direction from the normal range are given scores 1, 2 or 3 depending on how far the value is from the normal range. The final score may be the sum of the score for each vital measurement.

TABLE 1

EXAMPLE MEWS

| Score | 4 | 3 | 2 | 1 | 0 | 1 | 2 | 3 | 4 |
|---|---|---|---|---|---|---|---|---|---|
| SBP | <70 | 70-80 | 81-90 | 91-100 | 101-180 | | >180 | | |
| HR (bpm) | <40 | 40-50 | | | 51-100 | 101-110 | 111-130 | 131-140 | >140 |
| RR (rpm) | <5 | 5-8 | | 9-14 | 15-19 | 20-29 | 30-35 | >35 | |
| Temp (° C.) | | | <35 | | 35.0-38.4 | | >38.5 | | |
| OSat | | <85 | 85-89 | 90-95 | >95 | | | | |

In one embodiment, 28 of the 125 features may be based on discrete MEWS bin features. For example, for each vital measurement a percentage of measurements of the six vital measurements within each bin is as shown in Table 1 above. Scores above and below the normal range are put into different bins. For example, if the heart rate measurements are 35, 39, 45, 40, 52 and 120 then there are two measurements (35, 39) with MEWS score 4 below the normal range, two measurements (40, 45) with MEWS score 3 below the normal range, one measurement (52) with MEWS score 0, one measurement (120) with MEWS score 2 above the normal range and zero measurements in all other ranges. So the corresponding feature vector is [2/6, 2/6, 1/6, 0, 1/6, 0, 0]. Similar features are constructed for each of the vitals except DBP.

In one embodiment, 1 feature of the 125 features may be based on a difference between the current timestamp and the first time timestamp in data for a patent. In one embodiment, 1 feature of the 125 features may be based on a difference between the current timestamp and a first timestamp after ICU admission. In one embodiment, 2 features of the 125 features may be based on an average rate at which vitals are measured since hospital admission and since ICU admission.

In one embodiment, each one of the lab measurements may contribute towards the 125 features. In other words, the 25 different lab measurements may contribute 25 features of the 125 features. In one embodiment, the age and gender may contribute to the final 2 features of the 125 features.

In one embodiment, the mortality prediction engine 210 may apply the n classifiers that were trained by the classifier training engine 208 to predict a mortality of a current patient (e.g., the current patient 150). In one embodiment, the mortality prediction engine 210 may perform the prediction at each i-th measurement timepoint using a corresponding i-th classifier. For example, the data collection and pre-processing engine 206 may collect data associated with the current patient 150 for an i-th measurement timepoint and pre-process the data to impute, or add, any missing data, as discussed above. The features used for analysis may be extracted from the data (e.g., the same 125 features used to train the classifiers).

The i-th classifier may be applied to the features that are extracted for the i-th measurement timepoint. The classifier may predict survival or mortality based on the features for the current patient 150. In one embodiment, the prediction may provide a percentage of falling into one of the two predictions (e.g., survival or mortality).

In one embodiment, a threshold value may be used to determine which outcome the classifier has predicted. For example, the outcome of survival or mortality having a percentage greater than 50% (or any other desired value such as 80%, 95%, and the like) may be determined to be the predicted outcome.

In one embodiment, the communication engine 212 may control the wired or wireless connections to the DB 106, the DB 108, the vital measurement devices 110, 112, 114, 116 and 118, and the HAS 120. For example, the communication engine 212 may monitor each communication session and manage the opening, maintaining and closing of each communication session.

Figure 3:
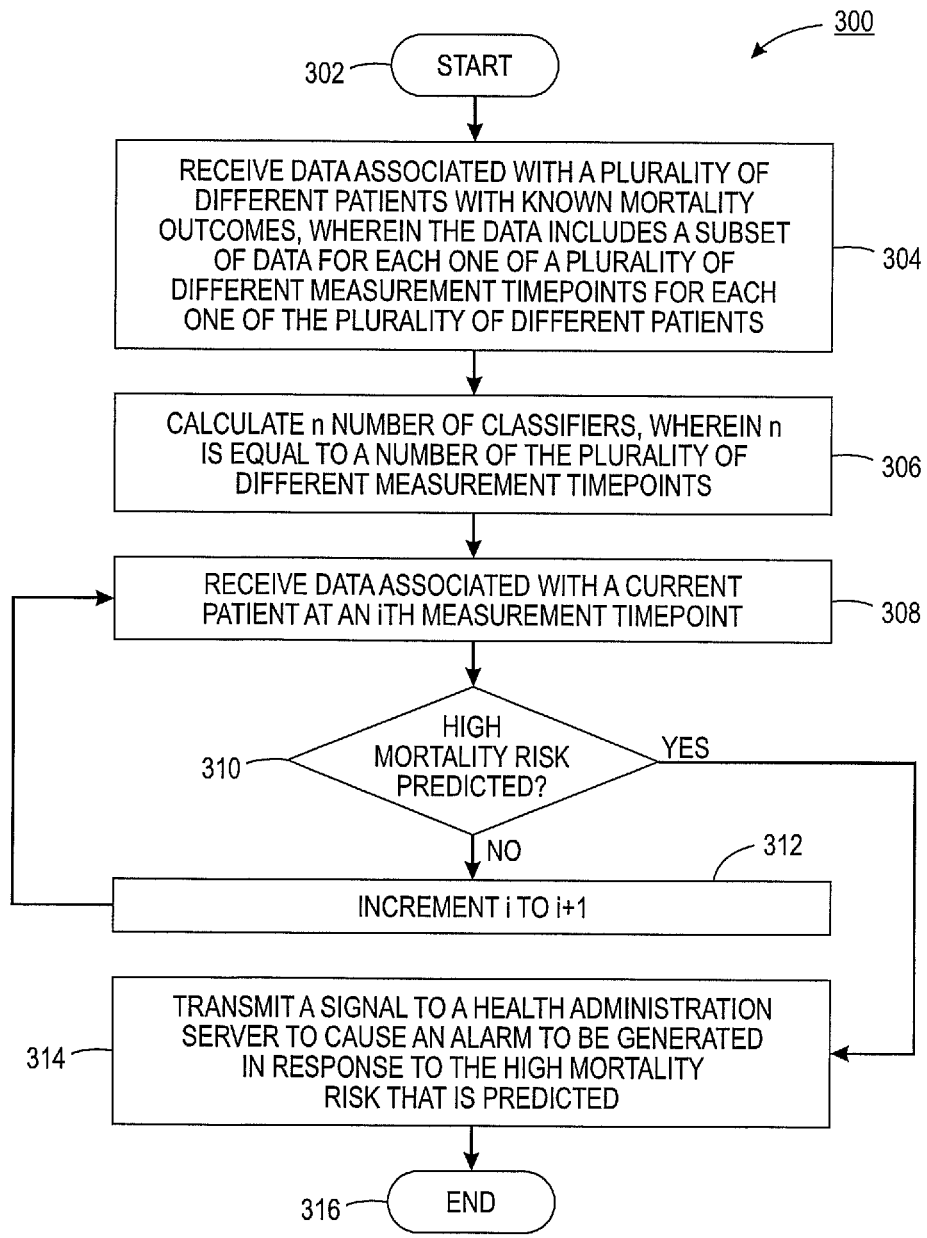
FIG. 3 illustrates a flowchart of an example method for predicting mortality of a current patient.
Figure 4:
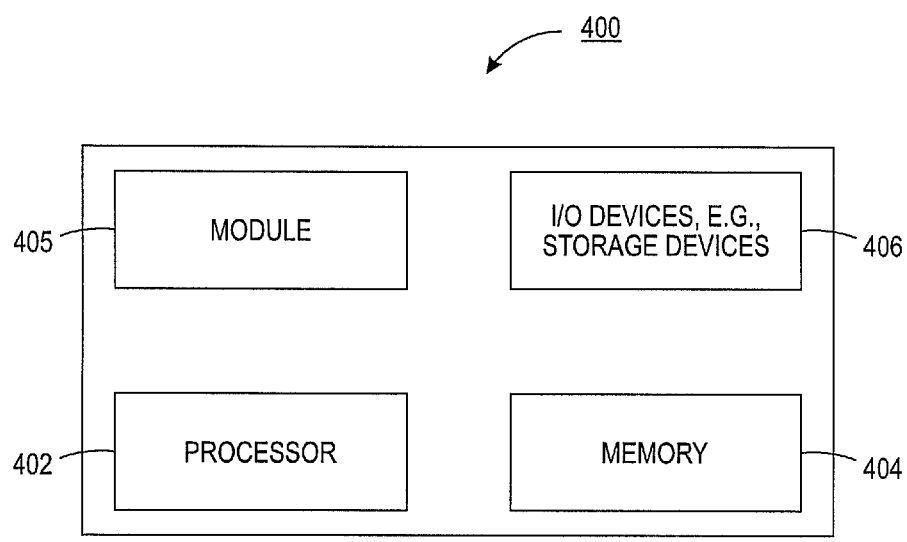
FIG. 4 illustrates a high-level block diagram of a computer suitable for use in performing the functions described herein.

FIG. 3 illustrates a flowchart of a method 300 for predicting mortality of a current patient. In one embodiment, one or more steps or operations of the method 300 may be performed by the AS 104 or a computer as illustrated in FIG. 4 and discussed below.

At block 302, the method 300 begins. At block 304, the method 300 receives data associated with a plurality of different patients with known mortality outcomes, wherein the data includes a subset of data for each one of a plurality of different measurement timepoints for each one of the plurality of different patients, wherein the data is received via a communication session to a plurality of vital measurement devices and a server storing lab measurements. For example, the data used to train the classifiers of the present disclosure can all be received via an automated connection or process. In other words, no manual observations are required to collect the data used to train the classifiers.

In one embodiment, the data may be pre-processed to add any missing values for a particular measurement timepoint. In one embodiment, a value for a previous measurement timepoint may be applied for the missing data of a current measurement timepoint when the value for the previous measurement timepoint is less than four hours old. In another embodiment, the missing data may be estimated using a MICE function.

At block 306, the method 300 may calculate n number of classifiers, wherein n is equal to a number of the plurality of different measurement timepoints. For example, the number of the plurality of different measurement timepoints may be determined based upon a highest number of measurement timepoints for a patient from the data that is collected in block 304. Thus, if the highest number of measurement timepoints was 20, then 20 classifiers would also be trained.

In one embodiment, each i-th measurement timepoint has a corresponding i-th classifier. Thus, a different classifier may be applied for each different measurement timepoint.

In one embodiment, the classifiers may be trained using a random forest function. For example, a random forest of 500 trees may be used. The classifiers may be trained based upon features that are identified within the data obtained in block 304. In one embodiment, the features may be extracted from each subset of the data that corresponds to a different measurement timepoint.

In one embodiment, the features may be based on a plurality of vital measurements, a plurality of lab measurements and demographic information of the subset of data selected from the data that is collected. The plurality of vital measurements may include a systolic blood pressure, a diastolic blood pressure, a respiration rate, a heart rate, an oxygen saturation and a temperature. The plurality of lab measurements may include arterial blood pH, partial pressure of carbon dioxide, partial pressure of oxygen, sodium, potassium, bicarbonate, blood urea nitrogen, serum creatinine, white blood cell count, hematocrit, platelet count, bilirubin, urine output, low density lipoprotein cholesterol, lactic acid, troponin I, troponin T, random blood glucose, fasting blood glucose, fraction of inspired oxygen, albumin, alkaline, phosphatase, alanine, high density lipoprotein cholesterol and magnesium. The demographic information may include an age and a sex of the current patient.

In one embodiment, the features may include 125 different features. The 125 different features may be based off of statistical values of the plurality of vital measurements, the plurality of lab measurements and the demographic information.

At block 308, the method 300 may receive data associated with a current patient at an i-th measurement timepoint. The features used to train the classifiers may be extracted from the data. For example, if the 125 features were used to classify the i-th classifier, then the same 125 features may be extracted from the data.

In one embodiment, if any data is missing, the missing data may be imputed similar to the preprocessing performed in block 304. For example, a value for the (i–1)-th measurement timepoint may be applied for the missing data of the i-th measurement timepoint when the value for the (i–1)-th measurement timepoint is less than four hours old. Alternatively, the missing data may be estimated using a MICE function.

At block 310, the method 300 may determine whether a high mortality risk is predicted. For example, the classifiers that are trained may be binary classifiers. That is, the classifiers may predict one of two outcomes, survival or mortality. In one embodiment, a percentage may be calculated for how likely the current patient will fall into one of the two outcomes.

In one embodiment, a threshold value may be used to predict which outcome the current patient is classified to fall into. For example, the threshold value may be 50%. Thus, if the percentage that the current patient will be a survivor is greater than 50%, then the current patient may be predicted to survive at the i-th measurement timepoint. Alternatively, if the percentage that the current patient will be a high mortality risk is greater than 50%, then the current patient may be predicted to have a high mortality risk at the i-th measurement timepoint.

If the answer to block 310 is no, then the current patient is predicted to survive at the i-th measurement timepoint. At block 312, the method 300 may increment i to i+1 and the method 300 may return to block 308. The method 300 may continue to loop between blocks 308, 310 and 312 as long as the current patient is predicted to survive for each i-th measurement timepoint.

However, if the answer to block 310 is yes, then the method 300 may proceed to block 314. At block 314, the method 300 may transmit a signal to a health administration server to cause an alarm to be generated in response to the high mortality risk that is predicted. In one example, the signal may include a percentage of being classified as a high mortality risk that may help determine what medical action should be taken for the current patient.

In one embodiment, the health administration server may be a nurse monitoring station that displays a current status of the current patients in the ICU. If the current patient is determined to be a high mortality risk, an alarm may trigger for the current patient at the health administration server. In response, one or more communication signals may be sent to endpoint devices of additional doctors or nurses to take immediate medical action.

In one embodiment, the signal may cause the health administration server to automatically schedule appointments for a particular lab, a particular operating room, automatically prescribe a medication, and the like. As a result, precious seconds can be saved from a nurse or doctor recognizing the alarm and manually scheduling the lab, the operating room, prescribing a particular medication, and the like. At block 316, the method 300 ends.

It should be noted that although not explicitly specified, one or more steps, functions, or operations of the method 300 described above may include a storing, displaying and/or outputting step as required for a particular application. In other words, any data, records, fields, and/or intermediate results discussed in the methods can be stored, displayed, and/or outputted to another device as required for a particular application. Furthermore, steps, functions, or operations in FIG. 3 that recite a determining operation, or involve a decision, do not necessarily require that both branches of the determining operation be practiced. In other words, one of the branches of the determining operation can be deemed as an optional step.

FIG. 4 depicts a high-level block diagram of a computer that can be transformed to into a machine that is dedicated to perform the functions described herein. As a result, the embodiments of the present disclosure improve the operation and functioning of the computer to improve methods for predicting mortality of a current patient, as disclosed herein.

As depicted in FIG. 4, the computer 400 comprises one or more hardware processor elements 402 (e.g., a central processing unit (CPU), a microprocessor, or a multi-core processor), a memory 404, e.g., random access memory (RAM) and/or read only memory (ROM), a module 405 for predicting mortality of a current patient, and various input/output devices 406 (e.g., storage devices, including but not limited to, a tape drive, a floppy drive, a hard disk drive or a compact disk drive, a receiver, a transmitter, a speaker, a display, a speech synthesizer, an output port, an input port and a user input device (such as a keyboard, a keypad, a mouse, a microphone and the like)). Although only one processor element is shown, it should be noted that the computer may employ a plurality of processor elements. Furthermore, although only one computer is shown in the figure, if the method(s) as discussed above is implemented in a distributed or parallel manner for a particular illustrative example, i.e., the steps of the above method(s) or the entire method(s) are implemented across multiple or parallel computers, then the computer of this figure is intended to represent each of those multiple computers. Furthermore, one or more hardware processors can be utilized in supporting a virtualized or shared computing environment. The virtualized computing environment may support one or more virtual machines representing computers, servers, or other computing devices. In such virtualized virtual machines, hardware components such as hardware processors and computer-readable storage devices may be virtualized or logically represented.

It should be noted that the present disclosure can be implemented in software and/or in a combination of software and hardware, e.g., using application specific integrated circuits (ASIC), a programmable logic array (PLA), including a field-programmable gate array (FPGA), or a state machine deployed on a hardware device, a computer or any other hardware equivalents, e.g., computer readable instructions pertaining to the method(s) discussed above can be used to configure a hardware processor to perform the steps, functions and/or operations of the above disclosed methods. In one embodiment, instructions and data for the present module or process 405 for predicting mortality of a current patient (e.g., a software program comprising computer-executable instructions) can be loaded into memory 404 and executed by hardware processor element 402 to implement the steps, functions or operations as discussed above in connection with the example method 300. Furthermore, when a hardware processor executes instructions to perform "operations," this could include the hardware processor performing the operations directly and/or facilitating, directing, or cooperating with another hardware device or component (e.g., a co-processor and the like) to perform the operations.

The processor executing the computer readable or software instructions relating to the above described method(s) can be perceived as a programmed processor or a specialized processor. As such, the present module 405 for predicting mortality of a current patient (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. More specifically, the computer-readable storage device may comprise any physical devices that provide the ability to store information such as data and/or instructions to be accessed by a processor or a computing device such as a computer or an application server.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method for predicting mortality of a current patient, comprising:
receiving, by a processor, data associated with a plurality of different patients with known mortality outcomes, wherein the data includes a subset of data for each one of a plurality of different measurement timepoints for each one of the plurality of different patients, wherein the data is received via a communication session to a plurality of vital measurement devices and a server storing lab measurements;
training, by the processor, classifiers based on a plurality of features and the plurality of features is extracted from the data associated with the subset of data for the each one of the plurality of different patients that is selected based on one or more maximum values and one or more minimum values for a systolic blood pressure and a heart rate, the plurality of features comprising a plurality of vital measurements, a plurality of lab measurements, and demographic information of the subset of data that is selected, wherein the plurality of vital measurements comprises a diastolic blood pressure and a modified early warning score (MEWS) of the systolic blood pressure, a respiration rate, the heart rate, an oxygen saturation, and a temperature and are based on functions comprising $(\Sigma(p \in P)p)/|P|$, $(\Sigma(n \in N)n)/|N|$, $|N|/(|P|+|N|)$, and $|P|/(|P|+|N|)$, where $v_i$ denotes a vital measurement at an i-th measurement timepoint for $t_i$, for a patient, P is a set of consecutive differences $(v_i-v_{i-1})$ where $v_i>v_{i-1}$ and N is a set of consecutive differences $(v_i-v_{i-1})$ where $v_i<v_{i-1}$;
calculating, by the processor, n number of classifiers from the classifiers that are trained, wherein n is equal to a number of the plurality of different measurement timepoints, wherein each one of the n number of classifiers is associated with a respective one of the plurality of different measurement timepoints and the each one of the n number of classifiers is trained with the subset of data of the respective one of the plurality of different measurement timepoints using a random forest function, wherein the plurality of different measurement timepoints comprise an instance when a particular set of measurements of the current patient are taken;
receiving, by the processor, data associated with the current patient at an i-th measurement timepoint;
predicting, by the processor, the current patient has a high mortality risk based on an output of an i-th classifier of the n number of classifiers for the i-th measurement timepoint, wherein the output is based on the i-th classifier processing the data associated with the current patient;
transmitting, by the processor, a signal to a health administration server to cause an alarm to be generated in response to the high mortality risk that is predicted; and
automatically executing, by the processor, an action in response to the alarm, wherein the action comprises scheduling an appointment for a particular lab or scheduling an operating room.

2. The method of claim 1, comprising:
preprocessing, by the processor, the data associated with the plurality of different patients with known mortality outcomes to add missing data.

3. The method of claim 2, wherein the preprocessing comprises:
applying, by the processor, a value for a previous measurement timepoint for the missing data of a current measurement timepoint when the value for the previous measurement timepoint is less than four hours old.

4. The method of claim 2, wherein the preprocessing comprises:
estimating, by the processor, the missing data using a multivariate imputation by chained equations (MICE) function.

5. The method of claim 1, wherein the plurality of lab measurements comprises arterial blood pH, partial pressure of carbon dioxide, partial pressure of oxygen, sodium, potassium, bicarbonate, blood urea nitrogen, serum creatinine, white blood cell count, hematocrit, platelet count, bilirubin, urine output, low density lipoprotein cholesterol, lactic acid, troponin I, troponin T, random blood glucose, fasting blood glucose, fraction of inspired oxygen, albumin, alkaline, phosphatase, alanine, high density lipoprotein cholesterol and magnesium.

6. The method of claim 1, wherein the demographic information comprises an age and a sex of the current patient.

7. The method of claim 1, comprising:
imputing, by the processor, missing data associated with the current patient at the i-th measurement timepoint.

8. The method of claim 7, wherein the imputing comprises:
applying, by the processor, a value for an (i−1)-th measurement timepoint for the missing data of the i-th measurement timepoint when the value for the (i−1)-th measurement timepoint is less than four hours old.

9. The method of claim 7, wherein the imputing comprises:
estimating, by the processor, the missing data using a multivariate imputation by chained equations (MICE) function.

10. The method of claim 1, wherein the transmitting comprises sending a percentage of being classified as a high mortality risk at each i-th measurement timepoint.

11. A non-transitory computer-readable medium storing a plurality of instructions, which when executed by a processor, cause the processor to perform operations for predicting mortality of a current patient, the operations comprising:
receiving data associated with a plurality of different patients with known mortality outcomes, wherein the data includes a subset of data for each one of a plurality of different measurement timepoints for each one of the plurality of different patients, wherein the data is received via a communication session to a plurality of vital measurement devices and a server storing lab measurements;
training classifiers based on a plurality of features and the plurality of features is extracted from the data associated with the subset of data for the each one of the plurality of different patients that is selected based on one or more maximum values and one or more minimum values for a systolic blood pressure and a heart rate, the plurality of features comprising a plurality of vital measurements, a plurality of lab measurements, and demographic information of the subset of data that is selected, wherein the plurality of vital measurements comprises a diastolic blood pressure and a modified early warning score (MEWS) of the systolic blood pressure, a respiration rate, the heart rate, an oxygen saturation, and a temperature and are based on functions comprising $(\Sigma(p \in P)p)/|P|$, $(\Sigma(n \in N)n)/|N|$, $|N|/(|P|+|N|)$, and $|P|/(|P|+|N|)$, where $v_i$ denotes a vital measurement at an i-th measurement timepoint for $t_i$, for a patient P is a set of consecutive differences $(v_i - v_{i-1})$ where $v_i > v_{i-1}$ and N is a set of consecutive differences $(v_i - v_{i-1})$ where $v_i < v_{i-1}$;
calculating n number of classifiers from the classifiers that are trained, wherein n is equal to a number of the plurality of different measurement timepoints, wherein each one of then number of classifiers is associated with a respective one of the plurality of different measurement timepoints and the each one of then number of classifiers is trained with the subset of data of the respective one of the plurality of different measurement timepoints using a random forest function, wherein the plurality of different measurement timepoints comprise an instance when a particular set of measurements of the current patient are taken;
receiving data associated with the current patient at an i-th measurement timepoint;
predicting the current patient has a high mortality risk based on an output of an i-th classifier of the n number of classifiers for the i-th measurement timepoint, wherein the output is based on the i-th classifier processing the data associated with the current patient;
transmitting a signal to a health administration server to cause an alarm to be generated in response to the high mortality risk that is predicted; and
automatically executing an action in response to the alarm, wherein the action comprises scheduling an appointment for a particular lab or scheduling an operating room.

12. The non-transitory computer-readable medium of claim 11, comprising:
preprocessing the data associated with the plurality of different patients with known mortality outcomes to add missing data.

13. The non-transitory computer-readable medium of claim 11, wherein the plurality of lab measurements comprises arterial blood pH, partial pressure of carbon dioxide, partial pressure of oxygen, sodium, potassium, bicarbonate, blood urea nitrogen, serum creatinine, white blood cell count, hematocrit, platelet count, bilirubin, urine output, low density lipoprotein cholesterol, lactic acid, troponin I, troponin T, random blood glucose, fasting blood glucose, fraction of inspired oxygen, albumin, alkaline, phosphatase, alanine, high density lipoprotein cholesterol and magnesium.

14. The non-transitory computer-readable medium of claim 11 wherein the demographic information comprises an age and a sex of the current patient.

15. A method for predicting mortality of a current patient, comprising:
receiving, by a processor, data associated with a plurality of different patients with known mortality outcomes, wherein the data includes a subset of data for each one of a plurality of different measurement timepoints for each one of the plurality of different patients, wherein the data is received via a communication session to a plurality of vital measurement devices and a server storing lab measurements;
training classifiers using 125 features obtained from a combination of different statistical values of six vital measurements, a plurality of lab measurements, and demographic information, wherein the six vital measurements comprise a diastolic blood pressure, a modified early warning score (MEWS) of a systolic blood pressure, a respiration rate, a heart rate, an oxygen saturation, and a temperature and are based on functions comprising $(\Sigma(p \in P)p)/|P|$, $(\Sigma(n \in N)n)/|N|$, $|N|/(|P|+|N|)$, and $|P|/(|P|+|N|)$, where $v_i$ denotes a vital measurement at an i-th measurement timepoint for $t_i$, for a patient, P is a set of consecutive differences $(v_i-v_{i-1})$ where $v_i>v_{i-1}$ and N is a set of consecutive differences $(v_i-v_{i-1})$ where $v_i<v_{i-1}$ and N is a set of consecutive differences $(v_i-v_{i-1})$ where $v_i<v_{i-1}$, wherein the plurality of lab measurements comprises arterial blood pH, partial pressure of carbon dioxide, partial pressure of oxygen, sodium, potassium, bicarbonate, blood urea nitrogen, serum creatinine, white blood cell count, hematocrit, platelet count, bilirubin, urine output, low density lipoprotein cholesterol, lactic acid, troponin I, troponin T, random blood glucose, fasting blood glucose, fraction of inspired oxygen, albumin, alkaline, phosphatase, alanine, high density lipoprotein cholesterol and magnesium, wherein the demographic information comprises an age and a gender;

calculating, by the processor, n number of binary classifiers from the classifiers that are trained, wherein n is equal to a number of the plurality of different measurement timepoints, wherein each one of the n number of classifiers is associated with a respective one of the plurality of different measurement timepoints and the each one of the n number of classifiers is trained with the subset of data of the respective one of the plurality of different measurement timepoints using a random forest function, wherein the plurality of different measurement timepoints comprise an instance when a particular set of measurements of the current patient are taken;

receiving, by the processor, data associated with the current patient at an i-th measurement timepoint;

extracting, by the processor, the 125 features from the data associated with the current patient;

predicting, by the processor, the current patient has a high mortality risk based on an output of an i-th binary classifier of then number of binary classifiers for the i-th measurement timepoint, wherein the output is based on the i-th binary classifier processing the data associated with the current patient;

transmitting, by the processor, a signal to a health administration server to cause an alarm to be generated in response to the high mortality risk that is predicted; and automatically executing, by the processor, an action in response to the alarm, wherein the action comprises scheduling an appointment for a particular lab or scheduling an operating room.

\* \* \* \* \*